United States Patent [19]

Brinkhous et al.

[11] 4,145,185

[45] Mar. 20, 1979

[54] REAGENTS FOR SCREENING TESTS AND BIOASSAY OF VON WILLEBRAND'S FACTOR (PLATELET AGGREGATING FACTOR) IN BLOOD PLASMAS

[75] Inventors: Kenneth M. Brinkhous, Chapel Hill; Marjorie S. Read, Durham, both of N.C.

[73] Assignee: Research Triangle Institute, Research Triangle Park, N.C.

[21] Appl. No.: 772,228

[22] Filed: Feb. 25, 1977

[51] Int. Cl.² .................... G01N 33/16; C09K 3/00; A61K 35/38

[52] U.S. Cl. .................. 23/230 B; 252/408; 424/3; 424/98

[58] Field of Search ............... 23/230 B; 252/408; 424/3, 98

[56] References Cited

U.S. PATENT DOCUMENTS

| | | | |
|---|---|---|---|
| 3,714,345 | 1/1973 | Hirata | 252/408 X |
| 3,715,427 | 2/1973 | Hirata | 252/408 X |
| 3,761,586 | 9/1973 | Matsumoto et al. | 424/98 |
| 3,819,605 | 6/1974 | Holleman et al. | 424/98 X |
| 3,869,548 | 3/1975 | Dabis | 424/98 X |
| 3,987,159 | 10/1976 | Spona et al. | 424/3 X |

FOREIGN PATENT DOCUMENTS 338221  6/1972  U.S.S.R. .................. 424/3

OTHER PUBLICATIONS

M. C. Boffa et al., Biochimica et Biophysica Acta, vol. 354, No. 2, pp. 275–290 (Jul. 1974).

J. P. Allain et al., J. Lab. Clin. Med., vol. 85, No. 2, pp. 318–328 (Feb. 1975).

N. MacKay et al., Effects of the Venom of the Rhinoceros Horned Viper (*Bitis nasicornis*) on Blood Coagulation Platelet Aggregation, and Fibrinolysis, J. Clin. Path., vol. 23, No. 9, pp. 789–796 (1970).

*Primary Examiner*—Joseph Scovronek
*Attorney, Agent, or Firm*—Cushman, Darby & Cushman

[57] ABSTRACT

Screening tests and bioassay of von Willebrand's factor (platelet aggregating factor) in human and animal blood plasma are effected using a reagent of blood platelets and snake venom having a positive platelet aggregating cofactor effect. The reagent and tests may also suitably employ dried blood platelets. The reagent may comprise dried platelets and either ristocetin or active snake venom as the platelet aggregating cofactor.

15 Claims, No Drawings

REAGENTS FOR SCREENING TESTS AND BIOASSAY OF VON WILLEBRAND'S FACTOR (PLATELET AGGREGATING FACTOR) IN BLOOD PLASMAS

BACKGROUND OF THE INVENTION

The present invention is concerned with certain improvements in test reagents for screen testing and the bioassay of von Willebrand's factor and platelet aggregating factor in human and animal plasmas as well as a new procedure therefor. The invention described herein was made in part during the course of work under a grant from the Department of Health Education and Welfare.

The chemistry and makeup of human and animal blood plasma has long been a topic of study in medical science. The coagulation of blood is a subject of much interest and complexity. One of the blood plasma proteins that is needed by the body for the prevention of hemorrhage is variously referred to as von Willebrand's factor (vWF), platelet aggregating factor (PAF), factor VIII:vWF, ristocetin cofactor, or as vWF/PAF. This plasma factor is reduced or absent in a bleeder disease, socalled von Willebrand's desease or vascular hemophilia, which occurs in both man and animals (e.g. dog and pig). This plasma factor is also altered in other disease states, and may be important in the development of atherosclerosis by recruiting platelets to the site of pre-atherosclerotic vascular injury.

Currently, there are two main procedures used in clinical laboratory diagnosis and blood plasma analysis for the determination of this plasma factor, sometimes referred to hereinafter as vWF/PAF. Both of these procedures utilize the following reagents:

(1) citrated plasma or other body fluid being tested for amount of vWF/PAF;

(2) a suspension of blood platelets for the determination of the presence or absence of platelet aggregation, and where present, its rate;

(3) a cofactor ristocetin which for certain plasma - platelet preparations (as human plasma with human platelets) is required in addition to vWF/PAF for platelet aggregation.

Ristocetin has been described by Howard et al (Ristocetin a new tool in the investigation of platelet aggregation. *Thromb. Diath. Haemorrh.* 26:362–69, 1971) as capable of precipitating fibrinogen from plasma in vitro as well as producing platelet aggregation. It is a substance of uncertain chemical structure isolated from *Nocardia lurida* and is available in lyophilized form from Abbott Laboratories, Chicago, Illinois. However, Fehlner et al have recently studied the structure of ristocetin and found that upon hydrolysis, a number of amino acids of unusual structure are obtained (see *Proc. Nat. Acad. Sci.*, Vol. 69, No. 9, pp. 2420–2421, Sept. 1972).

According to Weiss et al (Quantitative assay of a plasma factor deficient in von Willebrand's disease that is necessary for platelet aggregation. *J. Clin. Invest.* 52:2708–16, 1973) ristodetin is used in an aggregometer in order to quantitatively determine the von Willebrand's platelet aggregating factor. The "end point" employed according to this method is a tracing based on changes in light transmission through a platelet suspension upon the addition of vWF/PAF. Unfortunately this method is technically laborious and the number of samples which may be run in a half-day is very limited. Furthermore, tracings take time to record and require expensive instrumentation. The method further requires the use of washed platelet suspensions which are time consuming to prepare and many preparations are discarded due to spontaneous aggregation.

The second commonly used diagnostic method measures the macroscopic platelet aggregation time (i.e. determination of the rate of aggregation of a platelet suspension). Sarji et al (Nature of von Willebrand factor: a new assay and a specific inhibitor. *Proc. Nat. Acad. Sci. USA* 71:2937–41, 1974 the entire contents of which are incorporated herein by reference) describe the use of ristocetin in this simplified test procedure utilizing the macroscopic platelet aggregation time for the determination of von Willebrand's factor. Aggregation times commonly are in the neighborhood of 30 seconds or less and the end point is observed visually. The number of samples which can be run in a half-day greatly exceeds that of the aggregometry method of Weiss et al. Nonetheless, this method also suffers the technical problem of laborious preparation of platelets.

More recently, it has been discovered that platelets fixed with (para)formaldehyde could be used as readily as fresh platelets resulting in the advantage that a batch of fixed platelets could be prepared and preserved for use for a period of one to two months (see Allain et al - Platelets fixed with paraformaldehyde: a new reagent for assay of von Willebrand factor and platelet aggregating factor. *J. Lab. Clin. Med.* 85:318–28, 1975 which is incorporated herein by reference). The fixed platelets when employed in the macroscopic test of Sarji et al have been found to result in a shorter aggregation time using ristocetin as a cofactor than when fresh platelets are employed (i.e. 10–20 seconds as compared with 30 seconds). The fixed platelets have been shown to be equally as useful in the assay of platelet aggregating factor (PAF) in animal plasma which clumps human platelets. Platelet aggregating factor is an activity of the same plasma protein as von Willebrand factor of human plasma detected by ristocetin-induced aggregation of human platelets. The use of fixed platelets resulted in the additional advantage that they were insensitive to other platelet aggregating agents which might be present in the plasma sample being tested, such as thrombin or adenosine diphosphate or thromboxanes, prostaglandin derivatives.

However, two exceptions were encountered regarding the use of ristocetin cofactor reagent in the test for von Willebrand's factor and platelet aggregating factor. The first related to the ability of types of animal plasmas (e.g. pig and cow) to aggregate fresh or fixed human platelets without ristocetin. Secondly, certain plasmas such as dog would not aggregate either human or dog platelets if ristocetin were present, and thus no assay could be readily obtained on these plasmas.

Furthermore, it was found that both patients with von Willebrand's disease as well as with other diseases may acquire an inhibitor to the vWF/PAF, i.e. a plasma gamma globulin antibody. Both the procedures of Weiss et al and Sarji et al may be employed to detect presence of the inhibitor and by serially diluting the patients' plasma, the titer of the inhibitor can be determined with these tests.

Accordingly, it is the principle object of the present invention to provide a test reagent for the bioassay of von Willebrand's factor and platelet aggregating factor in blood plasmas which meets the requirements set forth above and obviates difficulties and disadvantages encountered with prior art test reagents.

A further specific object of the present invention is to provide a modify prior test reagent compositions thereby providing a more effective and accurate means of determining the von Willebrand's factor and platelet aggregating factor in human and animal blood plasmas.

Still yet a further object of the present invention is to provide a procedure for the accurate determination of von Willebrand's factor and platelet aggregating factor in human and animal blood plasmas.

Yet another object of the present invention is to provide for the inclusion of dried platelets as a reagent for the testing of vWF/PAF in human and animal blood plasmas.

These and other objects will be apparent from the description of the invention which follows hereinbelow.

DESCRIPTION OF THE INVENTION

Broadly stated, the above and other objects are realized by providing a test reagent comprising blood platelets and, as a cofactor for platelet aggregation, snake venom characterized as having a positive cofactor effect, for example *Bothrops jararaca* venom. As used herein, a positive cofactor effect is meant to refer to the ability of a venom which upon addition of blood platelets and plasma results in an aggregation or a clumping of the blood platelets in the presence of von Willebrand's factor and/or platelet aggregating factor within two minutes.

The invention further provides a procedure for the bioassay of von Willebrand's factor and platelet aggregating factor in human and animal plasmas by determining the rate of aggregation of a platelet suspension obtained upon the addition of human or animal blood plasma to a test reagent comprising blood platelets and a cofactor of snake venom having a positive cofactor effect.

According to the present invention, we have found that certain snake venoms, most notably that of *Bothrops jararaca* may be employed as a substitute for ristocetin in the vWF/PAF assay. The vWF/PAF cofactor activity (i.e. positive cofactor effect) may be partially isolated from the fibrinogen coagulant or thrombin-like activity of the venom by chromatography. We have found that the cofactor aggregating agent in venom provides the advantage that it has a broader spectrum of action than that obtained with ristocetin. Thus, the vWF/PAF of dog plasma is readily assayable using snake venom plus either dog or human platelets. We have found many combinations of plasma and platelets of different species which are reactive to the snake venom, but not to ristocetin, as cofactor.

We have found that the use of *Bothrops jararaca* venom is particularly well suited for the test reagent and procedures of the present invention. However, other snake venoms have been found to be effective and thus are contemplated including for example, as follows: *Bothrops alternatus, Bothrops neowiidis, Trimeresurus flavoviridis, A. rhodostoma, Bothrops atrox, Bothrops jararacussu,* and *Bothrops lansbergii*. These venoms may be obtained in their crude dehydrated form (i.e. air dried or lyophilized) from such commercial sources as Sigma Chemical, Silver Springs, or the Miami Serpentarium. The venom should be stored under refrigeration prior to use.

It has also been found that one may use a light-transmission apparatus to accurately time the rate of aggregation of platelet suspensions according to the method of Sarji et al. Thus, the present invention provides a means of obtaining the end-point mechanically instead of by direct observation of the platelet aggregation time. The platelet suspension is relatively opaque and with aggregation, increased light transmission occurs which may be recorded accurately.

The platelet preparations used for the tests according to the present invention may suitably be dried, and thus easily preserved thereby providing a more convenient reagent for the test than that employed heretofore. However, either freshly prepared platelet preparations or formaldehydefixed platelets may be dried and employed in the tests. Preferably fixed-dried platelets are employed. Such fixeddried platelets may be fixed with formaldehyde, (para)formaldehyde or glutaraldehyde by the procedure of Allain et al above.

In its broader aspects therefore, the test reagent for the bioassay of von Willebrand's factor and platelet aggregating factor in human and animal blood plasmas comprises human or animal blood platelets, which may be freshly prepared, fixed, and/or air dried or lyophilized together with as a cofactor for platelet aggregation, snake venom characterized as having a positive cofactor effect. The human or animal blood platelets may be freshly prepared and in suspension or may be formaldehyde-fixed. Human and animal plasmas to be tested are prepared according to conventional procedures to provide a citrated plasma which upon addition of the blood platelets and snake venom cofactor results in an aggregation or a clumping of the blood platelets in the presence of von Willebrand's factor and/or platelet aggregating factor.

The following examples are offered in order to more fully illustrate the invention, but are not to be construed as limiting the scope thereof.

EXAMPLE 1

Preparation of Snake Venom

*Bothrops jararaca* venom obtained from Sigma Chemical Company, was prepared as follows. 4 milligrams of the venom is weighed out and dissolved in 1 milliliter of imidazole buffered saline (0.84 M imidazole, 0.154 M NaCl) adjusted to pH of 7.3 and stored at $-20°$ C. in 0.1 ml aliquots (stock solution). For use in test procedures, 0.1 ml aliquots are diluted to 4 mls with buffered saline (test solution). It was found that upon storage for 27 days at $-20°$ C. the venom remained stable as a platelet aggregating cofactor. Longer storage periods of 6 months indicate similar stability. The venom was capable of aggregating human platelets within 10 to 12 seconds while human platelet-poor plasma was not clotted in 2-3 minutes.

EXAMPLE 2

Platelet Preparation

Human fixed platelets were prepared according to the procedure outlined by Allain et al above with formaldehyde. Human blood is drawn in acid citrate dextrose (ACD), 1 part ACD, to 6.6 parts blood. This is centrifuged at room temperature at 460 $\times$ g for 8 minutes and the platelet-rich plasma aspirated. The platelet-rich plasma is then centrifuged at room temperature at 750 $\times$ g for 8 minutes so as to button out the platelets. The platelet-poor plasma (PPP) is poured off and 5 to 10 mls of acid citrated saline (pH 6.5) is added. The platelet button is then resuspended with a pipette by a gentle drawing up and down of the wash solution. The platelets are then centrifuged again and twice washed. These washed platelets are then resuspended in 5 mls of 2% paraformaldehyde and permitted to stand for about 2 hours at room temperature. 5 mls of imidazole buffered saline (pH 6.5) are added and the suspension is spun at room temperature at 700 × g for 8 minutes. The supernatant is poured off and the platelets resuspended in imidazole buffered saline, pH 6.5. The platelets are centrifuged as before and washed twice more in imidazole saline pH 6.5. They are counted and stored at 4° C. in imidazole buffered saline at pH 6.5 at a concentration of 800,000/cmm.

EXAMPLE 3

Dog fixed platelets were prepared in accordance with the procedure of Example 2 with the following modifications. The washed dog platelets are resuspended in 5 mls of 0.75% paraformaldehyde and permitted to stand 24 hours at 4° C. 5 mls of imidazole saline pH 6.5 is added, and the platelets are then resuspended and centrifuged at room temperature at 700 × g for 8 minutes. The supernatant is poured off and the platelets washed three times in imidazole saline pH 6.5. Subsequently, the platelets are counted and stored at 4° C. in saline pH 6.5 at 800,000/cmm. The 0.75% paraformaldehyde solution is prepared from 4.5 mls of 4% paraformaldehyde plus 0.5 ml ACD diluted to 26.6 mls with 0.135 M $KH_2PO_4$.

EXAMPLE 4

Preparation of Air-Dried Platelets

A button of fixed human or dog platelets prepared according to the procedure of Examples 2 or 3 after being thrice washed is suspended in 5 ml solution of bovine crystalline albumin (50 mgm/ml citrated saline). The platelets are counted and adjusted to 800,000/cubic millimeter (cmm) with citrate-saline, albumin diluent.

2 ml aliquots of the prepared platelets are placed in glass vials and a stream of air is passed over the vials at room temperature for a period of 6 to 12 hours so as to dehydrate the platelets. The dehydrated platelets are then stored at 4° C. until ready for use and are stable for at least one week. The dehydrated platelets may be reconstituted in 2 ml. of either water or an imidazole or phosphate buffered saline (pH 7.3) at room temperature. The reconstituted platelets are stable at room temperature for at least 8 hours.

EXAMPLE 5

Preparation of Lyophilized Platelets

Platelet suspensions of fixed human or animal platelets according to Example 4 are frozen at temperatures from −20° to −70° C. for a period of 6 to 12 hours. These are then transferred to lyophilization apparatus (Virtis lyophilizer) for 6 hours. The lyophilized platelets are stored in vials at 4° C. until ready for use. When ready for use, the lyophilized platelets may be reconstituted in either water or buffer according to the method outlined in Example 4.

In the Examples below, plasma preparations were obtained from whole blood which had been anticoagulated with one part of 3.2% sodium citrate to 9 parts whole blood. The blood is spun at 4° C. for a period of 20 minutes at 900 × g and the platelet-poor plasma (PPP) taken from the top two-thirds is used immediately or else stored at −20° C. In some instances, ethylene diamine tetracetic acid was used as anticoagulant to prepare the platelet-poor plasmas. These plasmas are prepared from one part of 2% EDTA in saline with 9 parts of whole blood which is also spun at 4° C. for a period of 20 minutes at 900 × g in a similar fashion to the preparation of citrated plasma preparations. The macro platelet aggregating test is conducted in accordance with the procedures described by Sarji et al, supra, the entire contents of which are incorporated herein by reference. In each instance, the test tystem comprises 0.1 ml buffer, 0.1 ml PPP, 0.1 ml fixed platelets, and 0.1 ml of the snake venom having a positive cofactor effect. Control tests were done with a buffer substituted for PPP and/or venom. A stop watch is started with the addition of the venom, which is added last, and the tube is gently tapped until the first signs of aggregation appear at which time the time is recorded. The degree of aggregation is recorded as described by Brinkhous et al, "Macroscopic Studies of Platelet Aggregation", *Proceedings of the Society for Experimental Biology and Medicine*, V 98, pp. 379–383 (1958), the contents of which are incorporated by reference herein. In the data which follows relating to platelet aggregates 1+ indicates about 5 platelets per aggregate; 2+ indicates 10–25 platelets per aggregate; 3+ indicates 30 to 100 platelets per aggregate and 4+ refers to over 100 platelets per aggregate.

EXAMPLE 6

The air dried and lyophilized fixed platelets of Examples 4 and 5 were compared with fixed, undried platelets of Example 2 and the results are set forth in Table 1 below. The citrated plasmas employed in these tests from human subjects were obtained from a normal young adult. The severe von Willebrand's disease (vWD) citrated plasma was obtained from a patient having the disease. The animal plasmas were citrated and prepared from whole blood collected by venipuncture from a normal pig, a pig which was a carrier of vWD, a bleeder pig with severe vWD, and normal cow.

TABLE 1

| Platelet Drying Procedure | Plasma | Cofactor | Macroscopic Platelet Aggregation Time | vWF/PAF % |
|---|---|---|---|---|
| 1. Fixed; Air Dried | Human | | | |
| | Normal (1:1) | Ristocetin | 5", 4+ | 100 |
| | Normal (1:4) | Ristocetin | 10", 4+ | 25 |
| | vWD, severe | Ristocetin | >120" | <5 |
| | Animal | | | |
| | Bovine (1:4) | None | 6", 4+ | 25 |
| | Porcine normal (1:1) | None | 5", 4+ | 100 |
| | Porcine vWD carrier | None | 10", 4+ | 40 |
| | Porcine vWD | None | >120 " | <5 |
| 2. Fixed; Lyophilized | Human | | | |

TABLE 1-continued

| Platelet Drying Procedure | Plasma | Cofactor | Macroscopic Platelet Aggregation Time | vWF/PAF % |
|---|---|---|---|---|
| | Normal (1:1) | Ristocetin | 5", 4+ | 100 |
| | Normal (1:4) | Ristocetin | 12", 4+ | 25 |
| | vWD, severe | Ristocetin | >120 " | <5 |
| | Animal | | | |
| | Bovine (1:4) | None | 6", 4+ | 25 |
| | Porcine normal (1:1) | None | 5", 4+ | 100 |
| | Porcine normal (1:4) | | 9", 4+ | 25 |
| | Porcine vWD carrier (1:1) | None | | 40 |
| | Porcine vWD (1:1) | None | >60" | <5 |
| 3. Fixed; Not Dried | Human | | | |
| | Normal | Ristocetin | 5", 4+ | 100 |
| | vWD, severe | Ristocetin | >120 " | <5 |
| | Animal | | | |
| | Bovine (1:4) | None | 8.5", 4+ | 25 |
| | Porcine normal (1:1) | None | 8.5", 4+ | 100 |
| | Porcine vWD carrier (1:1) | None | 18", 4+ | 44 |
| | Porcine vWD | None | >60" | <5 |

From Table I, it can be seen that the dried, fixed human platelets, when used with normal human plasma and ristocetin, provide for rapid macroscopic aggregation times with 4+ platelet aggregates (i.e. 100 or more platelets per aggregate), which is the same as fixed undried platelets. By way of comparison, the severe vWD plasma effected no platelet aggregation in the 120 second observation period for any of the platelet preparations. Assay of vWF by serial dilution of plasma in accordance with the method described by Brinkhous et al (Assay of von Willebrand Factor in von Willebrand's Disease and Hemophilia: Use of a Macroscopic Platelet Aggregation Test. *Thrombosis Research* 6:267-272, 1975, the contents of which are incorporated herein by reference) resulted in comparable data with all platelet preparations (Note last column of Table 1).

EXAMPLE 7

Use of Snake Venom as a cofactor for Assay of vWF/PAF In Human Plasmas

The use of the venom from *Bothrops jararaca* as a cofactor for the assay of vWF in human plasmas was tested. Four separate platelet preparations were employed and the fixed or fixed dried platelets were prepared as in the preceding Example. The fresh platelets were isolated and washed as described in Example 2 without fixative (i.e., paraformaldehyde). The human plasmas were prepared as in the procedure of Example 6.

The venom used was dehydrated *B. jararaca* venom obtained from Sigma Chemicals, Lot 89B-1870. The stock solution and the test solution of venom were prepared and stored as in Example 1. The results are set forth in Table 2 below.

TABLE 2

| | Human Platelets | Human Plasma | Cofactor | Platelet Aggregation Macroscopic (sec., degree) | VWF* % |
|---|---|---|---|---|---|
| 1. | Fixed, Air Dried | Normal | B. jararaca | 11.5", 4+ | 100 |
| | | vWD, mild | B. jararaca | 26.0", 2+ | 28 |
| | | vWD, severe | B. jararaca | >120 ", — | <5 |
| 2. | Fixed, Lyophilized | Normal | B. jararaca | 10.5", 4+ | 100 |
| | | vWD, severe | B. jararaca | >120", — | <5 |
| 3. | Fixed | Normal | B. jararaca | 11", 4 + | 100 |
| | | vWD, severe | B. jararaca | >120", — | <5 |
| 4. | Fresh | Normal | B. jararaca | 15", 4+ | 100 |
| | | vWD, severe | B. jararaca | >120", — | <5 |

*Brinkhous et al assay method used.

As can be seen, normal plasma with *B. jararaca* cofactor resulted in prompt aggregation of all of the platelet preparations. Insofar as the control tests were concerned employing a buffer instead of venom, no platelet aggregation was observed. The results are set forth in the last column of Table 2. Aggregometry was also used with all four types of platelets and the venom. With normal plasma, there was a greater increase in light transmission as the platelets aggregated in the presence of the venom, unlike with severe vWD plasma in which no change was observed.

EXAMPLE 8

Animal Platelets With Venom as cofactor

In this Example, platelets obtained from four animal species were tested for reactivity in the vWF/PAF test systems. The platelets which were tested were obtained from horse, cow, pig and dog and in each case were formaldehydefixed and either air dried or lyophilized and tested with normal human plasmas. Consistently, dog platelet preparations gave the shortest aggregation times and the platelets obtained from the other species were found to be reactive with the venom as the cofactor. The results with dog platelets are set forth in Table 3.

TABLE 3 a) Assay of Human Plasma with Dog Platelets

| Human Plasma | Platelets | Cofactor | vWF % |
|---|---|---|---|
| Normal | Fixed dog | Venom | 100 |
| | Fixed dried dog | Venom | 100 |
| | Fixed dog | Ristocetin | no aggregation |
| vWD, severe | Fixed dog | Venom | <5 |
| | Fixed dried dog | Venom | <5 |
| vWD, mild | Fixed dog | Venom | 20 |
| vWD, mild | Fixed dog | Venom | 37 |
| vWD, mild | Fixed dried dog | Venom | 28 | b) Serially Diluted Normal Human Plasma and Aggregation of Fixed Dried Dog Platelets with Venom Human Plasma

TABLE 3-continued

| Dilution | Macroscopic Aggregation Time |
|---|---|
| 1:1 | 10", 4+ |
| 1:2 | 15", 4+ |
| 1:4 | 18", 4+ |
| 1:8 | 26", 3-4+ |

EXAMPLE 9

A single reagent of dried platelets, either human or animal and cofactor, either ristocetin or snake venom having a positive cofactor effect was prepared. The single reagent consisted of reconstituted lyophilized mixture of cofactor, either ristocetin or venom and fixed platelets, either human or animal for the bioassay of human or animal blood plasma vWF. The results are set forth in Table 4 below. In those instances were ristocetin was employed as the cofactor, the procedure for the preparation of the single reagent included the preparation of fixed human platelets in accordance with Example 2, 1 ml of which was mixed with 1 ml of ristocetin (2.4 mgm/ml normal saline) which is frozen and lyophilized. The reagent is stored at 4° C. until ready for use at which time it is reconstituted with distilled water for the test, employing 0.2 ml reconstituted single reagent plus 0.1 ml buffer having a pH of 7.4 with 0.1 ml diluted human plasma, normal or vWF deficient.

When using venom as a cofactor, the procedure for the preparation of the single reagent was as follows. To a series of 10 × 75 mm test tubes were added 0.1 ml buffer of pH 7.4 and 0.1 ml fixed platelets in albumin. The tubes were placed in an ice-salt bath until the mixture was frozen. Then, layered on the frozen contents was 0.1 ml chilled Bothrops jararaca venom (100 ug/ml in imidazole buffered saline, pH 7.35). The mixture is then replaced in an ice-salt bath until frozen and stored at −20° C. until placed in a lyophilizer wherein it is lyophilized. The lyophilized reagent is then reconstituted with 0.3 ml distilled water immediately prior to use.

TABLE 4

| Single Reagent | Plasma | Aggregation Times |
|---|---|---|
| 1. Dried human platelets plus venom cofactor | Human | |
| | 1:1 | 11", 4+ |
| | 1:4 | 19", 4+ |
| | Dog | |
| | 1:1 | 6", 4+ |
| | 1:4 | 10", 4+ |
| 2. Dried human platelets plus ristocetin cofactor | Human 80 | |
| | 1:1 | 6", 4+ |
| | 1:4 | 10", 4+ |
| | Dog | |

TABLE 4-continued

| Single Reagent | Plasma | Aggregation Times |
|---|---|---|
| | 1:1 | No Aggregation |
| | 1:4 | No Aggregation |
| 3. Dried dog platelets plus venom cofactor | Human | |
| | 1:1 | 20", 4+ |
| | 1:4 | 30", 4+ |
| | Dog | |
| | 1:1 | 7", 4+ |
| | 1:4 | 12"4+ |

The use of fixed frozen platelets and frozen venom for testing for the vWF/PAF was investigated. Fixed platelets were prepared in accordance with the procedure described by Allain et al described above. Platelets were in suspension at a concentration of 800,000/mm$^3$ and were frozen at −20° C. The frozen platelets were then thawed rapidly in a 37° C. water bath and used in the vWF testing procedure for a period of 4 hours. In a similar manner, the venom was frozen and the results of these tests using the procedure of macroscopic aggregation time screening are set forth in Table 6 below.

TABLE 6

| Fixed Platelets | Freezing Temperature Cofactor | Plasma in vWF/PAF test | | Aggregation Time (sec) |
|---|---|---|---|---|
| Human | −20° C. | Ristocetin | Human, 1:1 | 5", 4+ |
| | | Venom | Human, 1:1 | 10", 4+ |
| | | None | Bovine, 1:1 | 5", 4+ |
| | | None 1 | Porcine, 1:1 | 7", 4+ |
| Dog | −20° C. | Ristocetin | Human, 1:1 | No aggregation, 60" |
| | | Venom | Human, 1:1 | 10", 4+ |
| | | None | Human, 1:1 | No aggregation, 60" |
| | | Venom | Dog, 1:1 | 4", 4+ |
| | | None | Dog, 1:1 | No aggregation, 60" |
| | | Venom | Bovine, 1:4 | 5", 4+ |
| | | None | Bovine, 1:4 | No aggregation, 60" |
| | | Venom | Pig, 1:1 | 5", 4+ |
| | | None | Pig, 1:1 | No aggregation, 60" |

From the foregoing Examples, it is clear that the use of snake venom having a positive cofactor effect provides a "broadspectrum" cofactor enabling the assay of von Willebrand's factor and platelet aggregating factor (vWF/PAF) in combinations of plasma and platelets from different species. Thus, animal platelets may be readily substituted for human platelets in clinical laboratory diagnostic and research studies for human vWF/PAF when using snake venom having a positive effect as the cofactor. This results of course in a considerable savings of time and expense.

Furthermore, it is clear that dehydrated fresh or fixed human platelets may be readily substituted for fresh or human fixed platelets in the assay procedure for vWF/PAF. Thus, by the use of dried platelets, a stable reagent is readily available in dry form for the test.

Of significant note is the fact that animal platelets may be fixed and dried and substituted for human platelets in the vWF/PAF assay procedure when using snake venom cofactor of the present invention. Thus, the present invention provides for the first time that fixed animal platelets may be employed for human vWF/PAF assays.

Further in screening tests for von Willebrand's disease with platelet-rich plasma, in which platelets aggregate on addition of the ristocetin cofactor, the use of venom with cofactor effect likewise would aggregate platelets in normal platelet-rich plasma but not in von Willebrand's disease plasma.

It will be appreciated that various modifications may be made to the invention as described above. Thus, while the invention has been described with particular reference to the use of *Bothrops jararaca* venom, other snake venoms may also be used.

In this regard, we have found the following venoms suitable for use in the present invention:

*Bothrops jararaca*
*Bothrops alternatus*
*Bothrops neowiidis*
*Trimeresurus flavoviridis*
*A. rhodostoma*
*Bothrops atrox*
*Bothrops jararacussu*
*Bothrops lansbergii*

Of the foregoing venoms, the *Bothrops jararaca, alternatus* and *neowiidis* exhibited a strong effect (i.e. rapid aggregation 4+ reaction - 100 or more platelets per aggregate - with normal undiluted and diluted plasma). The *Trimeresurus flavoviridis* and *A. rhodostoma* exhibited a weak effect (i.e. slow aggregation, 2+ reaction - 10-20 platelets per aggregate - with normal plasma and freshly prepared reagents). The *Bothrops atrox, jararacussu* and *lansbergii* venoms exhibited an aggregating effect but with positive controls with the vWD plasma. Venom from *C. durissus* and *C. terrificus* (each obtained from Silver Springs) were tested but found to provide no aggregation.

Furthermore, the present inventions may comprise, consist of or consist essentially of the hereinbefore recited components and procedures.

The invention being thus described, it will be obvious that the same may be varied further in a number of ways. Such variations are not to be regarded as a departure from the spirit and scope of the invention, and all such modifications as may be apparent to those skilled in the art are intended to be included herein.

We claim

1. A test reagent for the bioassay of von Willebrand's factor and platelet aggregating factor in blood plasmas comprising blood platelets and a snake venom characterized as having a positive cofactor effect for platelet aggregation.

2. The test reagent of claim 1 wherein said venom is obtained from a snake selected from the species *Bothrops jararaca, Bothrops alternatus, Bothrops neowiidis, Trimeresurus flavoviridis, A. rhodostoma, Bothrops atrox, Bothrops jararacussu,* and *Bothrops lansbergii.*

3. The test reagent of claim 2 wherein said species is selected from *Bothrops jararaca, Bothrops alternatus, Bothrops neowiidis, Trimeresurus flavoviridis,* and *A. rhodostoma.*

4. The test reagent of claim 2 wherein said species is selected from *Bothrops jararaca, Bothrops alternatus,* and *Bothrops neowiidis.*

5. The test reagent of claim 1 wherein said venom is *Bothrops jararaca* venom.

6. The test reagent of claim 1 wherein said platelets are fixed.

7. The test reagent of claim 6 wherein said platelets are dried.

8. A test reagent for the bioassay of von Willebrand's factor and platelet aggregating factor in human and animal plasmas comprising fixed-dried blood platelets and, as a cofactor for platelet aggregation, a snake venom characterized as having a positive cofactor effect, or ristocetin.

9. The test reagent of claim 8 wherein said platelets are airdried.

10. The test reagent of claim 8 wherein said platelets are lyophilized.

11. A procedure for the bioassay of von Willebrand's factor in blood plasma which comprises determining the rate of aggregation of a platelet suspension effected by adding human or animal blood plasma to the test reagent of claim 1.

12. A procedure for the bioassay of von Willebrand's factor in blood plasma which comprises determining the rate of aggregation of a platelet suspension effected by adding blood plasma to the test reagent of claim 8.

13. In a method of determining the degree of platelet aggregation in blood plasma wherein a suspension of blood platelets and a cofactor for platelet aggregation are added to the plasma to be tested, the improvement which comprises using snake venom characterized as having a positive cofactor effect as a cofactor for platelet aggregation.

14. In a method of determining the degree of platelet aggregation in human and animal plasma wherein a suspension of blood platelets and a positive cofactor for platelet aggregation are added to the plasma to be tested, the improvement which comprises using blood platelets which have been air dried or lyophilized.

15. A procedure for the bioassay of von Willebrand's factor in blood plasma which comprises determining the rate of aggregation of a platelet suspension by adding to human or animal blood plasma blood platelets and a snake venom characterized as having a positive cofactor effect for platelet aggregation.

* * * * *